(12) United States Patent
Moon et al.

(10) Patent No.: US 6,403,848 B1
(45) Date of Patent: Jun. 11, 2002

(54) PREPARATION OF HEXAFLUOROPROPYLENE FROM THE PYROLYSIS OF TRIFLUOROMETHANE AND TETRAFLUOROETHYLENE

(75) Inventors: Dong Ju Moon; Hong Gon Kim; Byoung Sung Ahn; Moon Jo Chung; Young Soo Kwon, all of Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 09/820,631

(22) Filed: Mar. 30, 2001

(30) Foreign Application Priority Data

Nov. 11, 2000 (KR) .......................... 2000-66976

(51) Int. Cl.$^7$ .............................................. C07C 17/02
(52) U.S. Cl. ....................................... 570/159
(58) Field of Search .......................... 570/159

(56) References Cited

U.S. PATENT DOCUMENTS

| | | |
|---|---|---|
| 2,759,983 A | 8/1956 | Waddell |
| 3,009,966 A | 11/1961 | Hauptschein et al. |
| 3,446,858 A | 5/1969 | Shingu et al. |
| 4,849,554 A | 7/1989 | Cresswell et al. |
| 4,898,645 A * | 2/1990 | Voight .......................... 570/159 |

FOREIGN PATENT DOCUMENTS

EP    0 287 219    10/1988

OTHER PUBLICATIONS

Moon, D.J., et al. "Synthesis of Hexafluoropropylene from the pyrolysis of R23", Applied Chemistry, vol. 4, No. 1, pp. 105–108 (May 2000) published at the Korean Society of Industrial and Engineering Chemistry, 2000's Annual Conference (Spring Session) May 12–13, 2000.

S.F. Politanskii, "Thermal Conversion of Fluoromethanes", translated from Kinetika I Kataliz, vol. 10, No. 3, pp. 500–505, May–Jun., 1969.

* cited by examiner

*Primary Examiner*—Alan Siegel
(74) *Attorney, Agent, or Firm*—Fitzpatrick, Cella, Harper & Scinto

(57) ABSTRACT

The present invention relates to a process for preparing hexafluoropropylene($CF_3CF=CF_2$, HFP) from the pyrolysis of trifluoromethane($CHF_3$, R23) and tetrafluoroethylene ($C_2F_4$, TFE) and more particularly, to the process for preparing hexafluoropropylene from the pyrolysis of an admixture of R23 and TFE mixed in an appropriate molar ratio at below 900 which is lower than the conventional reaction temperature and longer residence time, after investigating the pyrolysis reaction of R23 and TFE by the computer simulation. The process for preparing HFP is performed by carefully controlling reaction temperature with heat balance resulted from an endothermic pyrolysis of R23 and an exothermic dimerization of TFE to prevent from carbon formation, recycling unreacted R23 and TFE in the product separated and purified from distillation column, adding fresh R23 additionally to keep an appropriate molar ratio of R23 and TFE, to improve a total yield of HFP and to minimize heat supply from outside.

12 Claims, 1 Drawing Sheet

Figure 1:
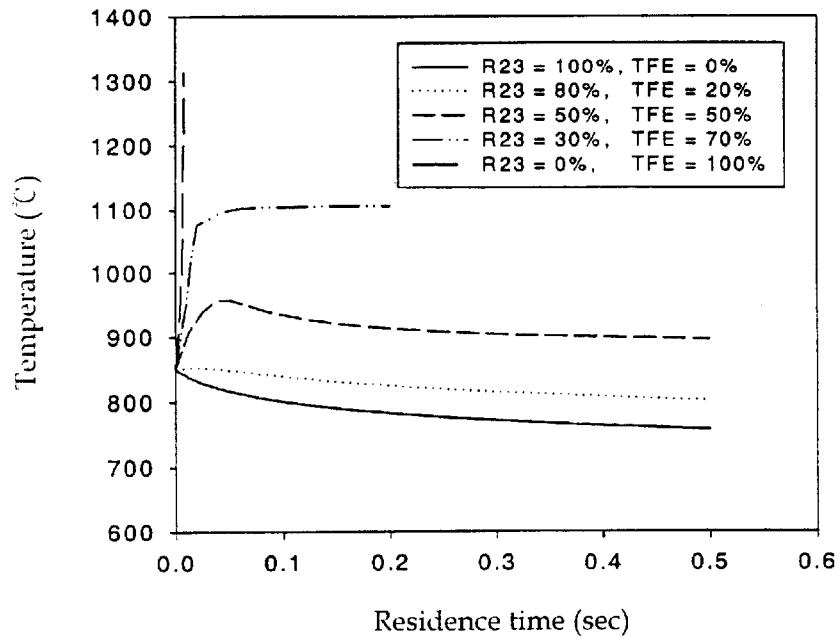

PREPARATION OF HEXAFLUOROPROPYLENE FROM THE PYROLYSIS OF TRIFLUOROMETHANE AND TETRAFLUOROETHYLENE

BACKGROUND OF THE INVENTION

1. Field of the Invention

The present invention relates to a process for preparing hexafluoropropylene($CF_3CF=CF_2$, HFP) from the pyrolysis of trifluoromethane($CHF_3$, R23) and tetrafluoroethylene ($C_2F_4$, TFE) and more particularly, to the process for preparing hexafluoropropylene from the pyrolysis of an admixture of R23 and TFE mixed in an appropriate molar ratio at below 900° C. which is lower than the conventional reaction temperature and longer residence time, after investigating the pyrolysis reaction of R23 and TFE by the computer simulation. The process for preparing HFP is performed by carefully controlling reaction temperature with heat balance resulted from an endothermic pyrolysis of R23 and an exothermic dimerization of TFE to prevent from carbon formation, recycling unreacted R23 and TFE in the product separated and purified from distillation column, adding fresh R23 additionally to keep an appropriate molar ratio of R23 and TFE, to improve a total yield of HFP and to minimize heat supply from outside.

2. Description of the Prior Art

As a monomer for preparing copolymers of fluorinated resins, the demand of HFP has been increased along with TFE. Conventional methods for preparing HFP are pyrolysis of difluorochloromethane($CHClF_2$, R22) (EP Patent No. 0,287,219 (1988) and U.S. Pat. No. 4,849,554 (1989)), pyrolysis of TFE and octafluorocyclobuthane($C_4F_8$, RC318) (U.S. Pat. No. 3,446,858 (1969)), pyrolysis of polytetrafluoroethylene(PTFE) (U.S. Pat. No. 2,759,983 (1956)), and pyrolysis of R23 (U.S. Pat. No. 3,009,966 (1961)).

The process of preparing HFP by the pyrolysis of R22 has low selectivity to HFP due to high selectivity of TFE formation and further, it is difficult to separate pure HFP from an azeotropic mixture of R22 and HFP. The pyrolysis of TFE to produce HFP suffers from a low selectivity to HFP because it mainly produces RC318. The pyrolysis of PTFE has complicate process wherein TFE is first prepared by pyrolysis of R22 and then polymerized to produce PTFE, followed by the pyrolysis thereof. And further, even if the selectivity to HFP is higher than that from the pyrolysis of R22 or TFE, it is an undesirable method because of expensive unit price.

Another method to produce TFE and HFP has been reported by Hauptschein and Fainberg (U.S. Pat. No. 3,009,966 (1961)). HFP is prepared by the pyrolysis of R23 at a temperature range of 700 to 1,500° C. and a residence time of 0.5 to 0.001 sec. Unreacted R23 and TFE, after separating form the product, are recycled to increase the selectivity to HFP. However, it suffers from the disadvantage of carbon formation as a side-reaction hindering the original pyrolysis, because this pyrolysis has to be performed at a high temperature above 900° C. This reaction requires continuous supply of heat from outside, which is expensive, and the temperature range is too broad during the reaction because it is difficult to control the reaction temperature. Politanskii et al. has reported that R23 is decomposed to carbene($:CF_2$) and HF (S. F. Poltanskii and V. U. Shevchuk, *Kinetika I Kataliz*, 9, 496 (1968)) and the pyrolysis reaction of R23 is an endothermic reaction, which requires continuous supply of heat from outside to keep the temperature above 900° C.

On the other hand, the dimerization of TFE is an exothermic reaction which requires continuous removal of heat. Therefore, when the pyrolysis of R23 is performed at above 1000° C., predominant byproduct TFE undergoes drastic dimerization and thereby, generates heat. As a result of this, the reaction temperature rapidly increases and it can be almost impossible to control the reaction temperature. Hauptschein and Fainberg have performed the pyrolysis reaction in the broad temperature range of from 700 to 1500° C. because of the drawback of controlling the reaction temperature resulted from an endothermic pyrolysis of R23 and an exothermic dimerization of TFE byproduct. However, when the reaction temperature is above 1000° C. in the pyrolysis of R23 to produce HFP, carbon formation reaction is predominately proceeded. So it is difficult to control the reaction temperature as well as to prevent from carbon formation.

SUMMARY OF THE INVENTION

Therefore, an object of the present invention is to provide an improved process for preparing HFP from the pyrolysis of an admixture of R23 and TFE mixed in an appropriate molar ratio, which is derived from the computer simulation of the pyrolysis of R23 and TFE for estimating an appropriate total heat calculated from an endothermic pyrolysis of R23 and an exothermic dimerization of TFE, to stabilize the reaction temperature.

Another object of the present invention is to perform the pyrolysis of said admixture at a temperature below 900° C. and a residence time of 0.1 to 5 to improve in controlling the reaction temperature and to prevent from carbon formation to produce HFP.

Another object of the present invention is to recycle unreacted R23 and TFE separated and purified from the product and to add fresh R23 for controlling an appropriate molar ratio of R23/TFE in order to obtain a high yield of HFP and to minimize heat supply from outside.

And further object of the present invention is to maximize the production of HFP from the pyrolysis of R23 and TFE for industrial scale based on the result of small scale obtained from the above conditions.

DETAILED DESCRIPTION OF THE INVENTION

In the present invention, it is characterized in that hexafluoropropylene is prepared from the pyrolysis of the mixture of trifluoromethane and tetrafluoroethylene mixed in the molar ratio of R23/TFE of 0.25 to 10 under the pyrolysis reaction conditions of R23 such as a reaction temperature of 750 to 950° C. and a residence time of 0.1 to 5 sec.

The present invention is described in more detail as set forth hereunder.

The present invention requires the computer simulation to investigate the pyrolysis of R23 for more efficient performance of the reaction. The pyrolysis reaction of R23 is an endothermic reaction, which requires continuous supply of heat from outside even at the temperature above 900° C., while the dimerization of TFE is an extreme exothermic reaction, which requires continuous removal of heat.

Therefore, the present invention requires the process to estimate the reaction conditions through the computer simulation for the adiabatic reaction condition, because the reaction temperature can be controlled by supplying both R23 and TFE in an appropriate ratio to a reactor. FIG. 1 shows the estimated result for the effect of temperature verses residence time for different molar ratio of R23 and TFE. As shown in FIG. 1, it indicates that the reaction temperature is rapidly increased at above 850° C., where the pyrolysis of R23 occurs, due to dimerization of TFE which is an exothermic reaction and thus, it is almost impossible to control the reaction temperature.

Based on the result of said computer simulation, it can be expected to perform the pyrolysis reaction of an a mixture of R23 of 50 to 80 mole % and TFE of 20 to 50 mole % to produce HFP by stabilizing the reaction temperature.

Therefore, the present invention provides an effective process for preparing HFP based on the best reaction conditions estimated through the computer simulation for the pyrolysis of an admixture of R23 and TFE.

Figure 2:
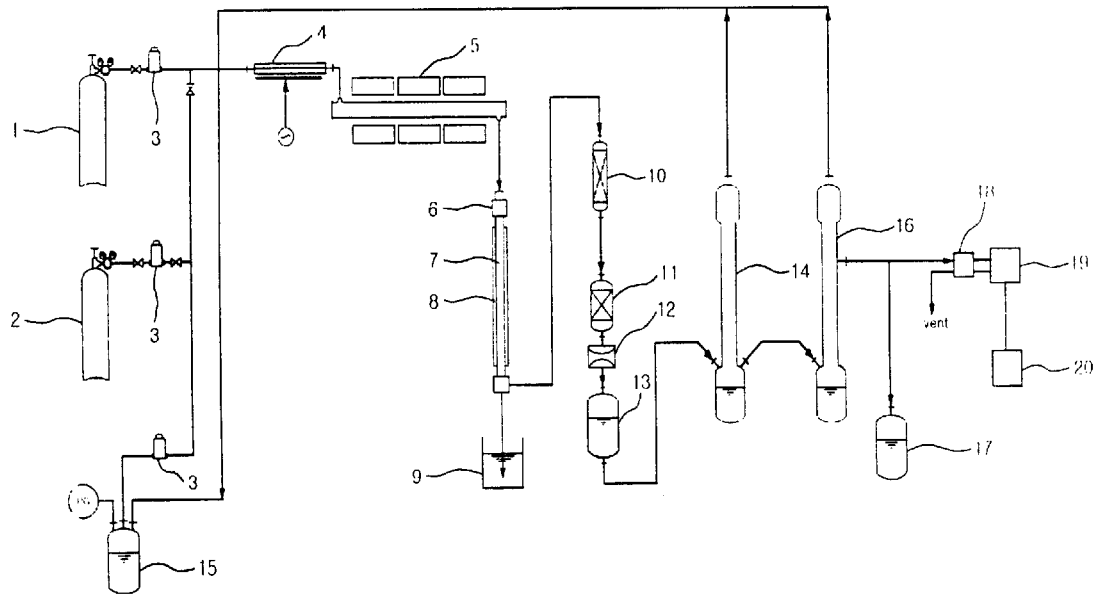

FIG. 2 shows the pyrolysis system with the pyrolysis of R23 and the purification for industrial applications. The present invention is characterized by the apparatus of FIG. 2 for the pyrolysis of R23 and TFE. It is important to apply an appropriate molar ratio of R23 and TFE to the reactor for the pyrolysis of an admixture of R23 and TFE. The present invention is also to provide maximum production of HFP by recycling unreacted R23 and TFE and stabilizing the reaction temperature between an endothermic pyrolysis of R23 and an exothermic dimerization of TFE.

The pyrolysis of the present invention is performed at a reaction temperature of 750 to 950° C., preferably 800 to 900° C. and a residence time of 0.1 to 5 sec, preferably 0.1 to 2 sec. If the reaction temperature is below 750° C., the production of HFP is low. On the other hand, if it is above 950° C., the formation of TFE increases and activates the dimerization of TFE and thus, it can be difficult to control the reaction temperature so that the production of HFP becomes low.

The preferable molar ratio of R23/TFE is in the range of 0.25 to 10, more preferably 1 to 4. If it is lower than 0.25, it activates the dimerization of TFE so that the reaction temperature can rapidly increase. If it is higher than 10, it requires additional heat supply from outside for the pyrolysis of R23.

The process of the present invention maximizes the production of HFP under the reaction conditions described above by using the apparatus of FIG. 2.

The apparatus for the pyrolysis of R23 and purification of IFP is comprised with a R23 cylinder (1), a TFE cylinder (2), a mass flow controller (3), a pre-heater (4), a reactor (5), process water (6), a quenching column (7), condensing water (8), an acid reservoir (9), an acid washing column (10), a diaphram gas compressor (11), a dryer (12), a product reservoir (13), the first distillation column (14), a R23/TFE mixture reservoir (15), the second distillation column (16), a HFP tank (17), a 6-port sampling valve (18), a gas chromatograph (19), and a personal computer (20). Said reactor (5) is made of Inconel metal and is tube-type having an outer diameter of ¾ inches and a length of 1.5 m.

HFP in the present invention is prepared by, passing through the pyrolysis and purification systems in the sequence of the mass flow controller (3) of R23 or an admixture of R23 and TFE, the pre-heater (4), the reactor (5), the quenching column (7), the acid washing column (10), the diaphram gas compressor (11), the dryer (12), the distillation columns (14, 16), and the recycle circuit. Unreacted R23 and TFE are separated from the distillation columns (14, 16) and then stored in the R23/TFE mixture reservoir (15). This separated mixture of R23 and TFE is supplied to the reactor (5) and fresh R23 can be added to the reactor (5) to keep an appropriate molar ratio. This mixture is then performed for the pyrolysis reaction. As a result, this process maximizes the production of HFP and minimizes loss of heat by controlling the reaction temperature. The quenching column (7) is placed at the exit of the reactor and thereby prevents from the formation of solid polymer by quenching with water.

HF produced during the reaction can be removed by passing through the quenching column (7), dissolving in water and then neutralizing at the acid reservoir (9). And again, acid removed product is passed in the sequence of the acid washing column (10) to remove remained HF, the diaphram gas compressor (11), the dryer (12), a reboiler (not shown in FIG. 2) connected to the first distillation column (14). Unreacted R23 and TFE after the pyrolysis of R23 are separated at the first distillation column (14) and stored at the R23/TFE mixture reservoir (15). The compounds having high boiling point are distilled again at the second distillation column (16) to get the desired product with high purity. The product, HFP, is analyzed by gas chromatograph (5890 series Il, Hewllet Packard Inc.) (19) equipped with a poraplot Q capillary column (0.32 mm(OD)×25 m(L)). The gas chromatography is operated under the conditions of a GC detector temperature of 200° C., an injection temperature of 150° C., a temperature of column of 90° C. and a helium head pressure of 5 psig, The product is identified by GC/MS (HP 5890/5971) equipped with the same column. The apparatus is controlled by the personal computer (20).

The following examples are intended to be illustrative of the present invention and should not be construed as limiting the scope of this invention defined by the appended claims.

COMPARATIVE EXAMPLE 1

Based on the computer simulation, the pyrolysis of R23 was performed in the pyrolysis apparatus with an Inconel reactor having an outer diameter of ⅜ inches and a length of 1.5 m at the reaction conditions such as a reaction temperature of 1000° C., a R23 supplying rate of 1 l/min, a residence time of 0.36 second and a reaction pressure of 1 atm. A content of R23 at the exit of the reactor was 11.9%, and each content of TFE, HFP, and PFiB was 22.2%, 53% and 7.1%, respectively. Especially, perfluoroisobutylene(PFiB, $(CF_3)_2C=CF_2$), which was not considered in the computer simulation, was formed in a significant amount and other byproducts such as $CF_3CCCF_3$, $C_2F_3H$, $CF_3CHCF_2$ and $CF_3CF_2CFCF_2$ was also produced about 5.8%.

COMPARATIVE EXAMPLE 2

The pyrolysis of R23 was performed with the same procedure as that of Comparative Example 1 except decreasing the R23 supplying rate to 0.5 l/min. A content of R23 was 3.8% and each content of TFE, HFP, PFiB and other byproducts was 4.7%, 57.8%, 21.2% and 12.5%, respectively.

EXAMPLE 1

The pyrolysis of R23 was performed with the same procedure as that of Comparative Example 1 except decreasing the reaction temperature to 900° C. from 1000° C. A content of R23 was 44.5% and each content of TFE, HFP, PFiB and other byproducts was 27.9%, 22.9%, 0.8% and 3.9%, respectively.

EXAMPLE 2

The pyrolysis of R23 was performed with the same procedure as that of Comparative Example 1 except decreasing the R23 supplying rate to 0.25 l/min and increasing the residence time to 1.57 sec. A content of R23 was 11.1% and each content of TFE, HFF, PFiB and other byproducts was 8.6%, 60.6%., 11.6%, and 8.1%, respectively.

COMPARATIVE EXAMPLE 3

The pyrolysis of R23 was performed with the same procedure as that of Comparative Example 1 except supplying a steam/R23 molar ratio of 4. Unlike the pyrolysis of R23 without applying steam, R23 was decomposed mainly to $CO_2$, CO, $H_2$ and $CF_4$ as shown in Table 1.

COMPARATIVE EXAMPLE 4

The pyrolysis of R23 was performed with the same procedure as that of Comparative Example 3 but the reaction temperature was decreased from 1000° C. to 900° C. The content of each R23, TFE, HFP and PFiB was less than 1% as shown in Table 1 and R23 was also decomposed mainly to $CO_2$, CO, $H_2$ and $CF_4$. Therefore, it indicated that it was not preferred to supply steam in the pyrolysis of R23 to produce HFP.

EXAMPLE 3

The pyrolysis of R23 for industrial scale was performed by using the apparatus of FIG. 2 based on the result of the computer simulation and small scale experiment. R23 was supplied to the reactor at a rate of 10.13 l/min by using the mass flow controller. The pyrolysis was performed at an average reaction temperature of 880° C., a residence time of 2 sec and a reaction pressure of 1.13 $kg/cm^2$.

A content of R23 was 46.6% and each content of TFE, HFP, PFiB and other byproducts was 26.1%, 19.3%, 4.5% and 3.5%, respectively.

EXAMPLE 4

The pyrolysis for an admixture of R23 and TFE was performed instead of R23. An admixture of R23 of 80.5% and TFE of 19.5% were supplied to the reactor at a rate of 10.13 l/min by using the mass flow controller. The pyrolysis was performed at an average reaction temperature of 875° C., a residence time of 2 sec, and a reaction pressure of 1.13 $kg/cm^2$.

A content of R23 was 39.5% and each content of TFE, HFP, PFiB and other byproducts was 31.4%, 25.5%, 1.1% and 2.5%, respectively.

EXAMPLE 5

The pyrolysis for an admixture of R23 of 61% and TFE of 39% was performed instead of R23. The mixture of R23 of 61% and TFE of 39% was supplied to the reactor at a rate of 10.13 l/min by using the mass flow controller. The pyrolysis was performed at an average reaction temperature of 872° C., a residence time of 2 sec and a reaction pressure of 1.13 $kg/cm^2$.

A content of R23 was 33.7% and each content of TFE, HFP, PFiB and other byproducts was 34.7%, 28.5%, 1% and 2.1%, respectively.

EXAMPLE 6

The pyrolysis for an admixture of R23 of 49.5% and TFE of 50.5% was performed instead of that of R23. The mixture of R23 and TFE was supplied to the reactor at a rate of 10.13 l/min by using the mass flow controller. The pyrolysis was performed at an average reaction temperature of 878° C., a residence time of 2 sec and a reaction pressure of 1.13 $kg/cm^2$.

A content of R23 was 28% and each content of TFE, HFP, PFiB and other byproducts was 42.9%, 25.8%, 1.1% and 2.2%, respectively.

EXAMPLE 7

The pyrolysis for an admixture of R23 of 35.6% and TFE of 64.4% was performed instead of that of R23. The mixture of R23 and TFE was supplied to the reactor at a rate of 10.13 l/min by using the mass flow controller. The pyrolysis was performed at an average reaction temperature of 873° C. residence time of 2 sec and reaction pressure of 1.13 $kg/cm^2$.

A content of R23 was 24.4% and each content of TFE, HFP, PFiB and other byproducts was 49.3%, 23.7%, 0.8% and 1.8%, respectively.

The result of Examples 1 to 7 and Comparative Examples 1 to 4 was listed in Table 1. According to table 1, the selectivities of HFP and PFiB in the pyrolysis of R23 or admixture of R23 and TFE increased with increasing a residence time and that of TFE decreased. The selectivities of PFiB and other byproducts such as $CF_3CCCF_3$, $C_2F_3H$, $CF_3CHCH_2$, $CF_3CF_2CFCF_2$, $CF_3CF_3$ and $CF_4$ increased with increasing reaction temperature. Therefore, it is preferred to lower the reaction temperature and to shorten the residence time to minimize the production of PFiB having strong toxicity. And further it is preferred to supply an admixture of R23 and TFE mixed in an appropriate ratio into the reactor to maximize the production of HFP, to stabilize the reaction temperature and to minimize outside supply of heat. The process of the present invention is applicable to stabilizing the reaction temperature by controlling heat balance between an exothermic dimerization of TFE and an endothermic pyrolysis of R23 and to improving the production of HFP by recycling the unreacted R23 and TFE.

TABLE 1

The result of the pyrolysis of R23 or admixture of R23 and TFE

|  | Rate for supply (l/min) | Feed Composition % | | | Residence time (sec) | Average reaction temp. (° C.) | Product composition (GC %) | | | | |
| --- | --- | --- | --- | --- | --- | --- | --- | --- | --- | --- | --- |
|  |  | R23 | TFE | H$_2$O |  |  | R23 | TFE | HFP | PFiB | others* |
| Comp. Example |  |  |  |  |  |  |  |  |  |  |  |
| 1 | 1 | 100 | 0 | 0 | 0.36 | 1000 | 11.9 | 22.2 | 53 | 7.1 | 5.8 |
| 2 | 0.5 | 100 | 0 | 0 | 0.73 | 1000 | 3.8 | 4.7 | 57.8 | 21.2 | 12.5 |

TABLE 1-continued

The result of the pyrolysis of R23 or admixture of R23 and TFE

| | Rate for supply | Feed Composition % | | | Residence time | Average reaction temp. | Product composition (GC %) | | | | |
|---|---|---|---|---|---|---|---|---|---|---|---|
| | (l/min) | R23 | TFE | $H_2O$ | (sec) | (° C.) | R23 | TFE | HFP | PFiB | others* |
| 3 | 1 | 20 | 0 | 80 | 0.36 | 1000 | 0.5 | 0.3 | 0.2 | 0.0 | 99.0 |
| 4 | 1 | 20 | 0 | 80 | 0.36 | 900 | 1.0 | 0.5 | 1.0 | 0.5 | 97 |
| Example | | | | | | | | | | | |
| 1 | 1 | 100 | 0 | 0 | 0.36 | 900 | 44.5 | 27.9 | 22.9 | 0.8 | 3.9 |
| 2 | 0.25 | 100 | 0 | 0 | 1.57 | 900 | 11.1 | 8.6 | 60.6 | 11.6 | 8.1 |
| 3 | 10.13 | 100 | 0 | 0 | 2.0 | 880 | 46.6 | 26.1 | 19.3 | 4.5 | 3.5 |
| 4 | 10.13 | 80.5 | 19.5 | 0 | 2.0 | 875 | 39.5 | 31.4 | 25.5 | 1.1 | 2.5 |
| 5 | 10.13 | 61 | 39 | 0 | 2.0 | 872 | 33.7 | 34.7 | 28.5 | 1.0 | 2.1 |
| 6 | 10.13 | 49.5 | 50.5 | 0 | 2.0 | 878 | 28.0 | 42.9 | 25.8 | 1.1 | 2.2 |
| 7 | 10.13 | 35.6 | 64.4 | 0 | 2.0 | 873 | 24.4 | 49.3 | 23.7 | 0.8 | 1.8 |

*others: CO, $CO_2$, $H_2$, $CF_4$, $CF_3CF_3$, $CF_3CCCF_3$, $C_2F_3H$, $CF_3CHCF_2$, $CF_3CF_2CFCF_2$

COMPARATIVE EXAMPLE 5

The pyrolysis of R23 was performed in the small scale reactor under the reaction conditions such as a temperature of 1100° C., a residence time of 0.1 sec which was introduced by Hauptschein and Fainberg. The reaction pressure increased during the reaction process due to carbon deposits in the reactor, resulting the difficulty in controlling the reaction temperature. Besidies TFE and HFP, other byproducts such as $CF_4$, $C_2F_6$, $C_3F_8$ and PFiB were formed in significant proportion.

COMPARATIVE EXAMPLE 6

Preparation of HFP from the Pyrolysis of R22

The pyrolysis of R22 was performed in a superheated steam diluent pyrolysis system with an Inconel reactor having an outer diameter of ⅜ inches and a length of 0.7 m to produce HFP. R22 was supplied to the reactor at a rate of 3.82 kg/h by using the mass flow controller after preheating to 200° C. with a pre-heater. Oxygen-removed water was supplied to a steam generator at a rate of 7 kg/h to generate steam of 550° C. and then steam was applied into a super heating unit. Steam in the super heating unit was passed through heating coil to generate steam of high temperature above 900° C. and then sprayed to the reactor through a nozzle for the pyrolysis of preheated R22. The temperature of the super heating unit was kept at 738° C. The conversion of R22 was 70.5%, TFE of 95% and only HFP of 1.2% was produced.

COMPARATIVE EXAMPLE 7

Preparation of HFP from the Pyrolysis of TFE

TFE produced from the pyrolysis of R22 in Comparative Example 6 was separated and purified from the distillation column. After this, TFE was supplied with a rate of 0.5 kg/h to an Inconel reactor with an outer diameter of 2 cm and a length of 1.5 m at an average temperature of 490° C. under a pressure of 1.5 kg/cm². The conversion of TFE was 91.3% and the selectivities of HFP and $RC_{318}$ were 7.5% and 92%, respectively. In the pyrolysis of TFE at a temperature range of 400–600° C., the selectivity of HFP increased with increasing temperature. However, this process requires two steps, to which one is the pyrolysis of R22 and separation of TFE and the other is the pyrolysis of TFE to produce HFP. And thus, it results in expensive unlit price and difficulty in separation of an azeotropic mixture of R22 and HFP.

As described above, the present invention is to provide a process for preparing HFP with a high yield by carefully controlling the reaction temperature between an endothermic reaction of R23 and an exothermic reaction of TFE and by the recycling of unreacted R23 and TFE in the product. And further, it provides the increased conversion of R23 and production of HFP by applying constant appropriate ratio of R23 and TFE.

What is claimed is:

1. A process for preparing hexafluoropropylene (HFP) from the pyrolysis of trifluoromethane (R23) and tetrafluoroethylene (TFE) mixed in a R23/TFE molar ratio of 0.25 to 10 is performed by applying an apparatus for the pyrolysis of trifluoromethane and purification at a temperature range of 750 to 950° C. and a residence time of 0.1 to 5 sec.

2. The process for preparing hexafluoropropylene from the pyrolysis of trifluoromethane and tetrafluoroethylene according to claim 1, wherein unreacted trifluoromethane and tetrafluoroethylene in the product are recycled after separated and purified from a distillation column to a reactor.

3. The process for preparing hexafluoropropylene from the pyrolysis of trifluoromethane and tetrafluoroethylene according to claim 1, wherein fresh trifluoromethane is added additionally to keep an appropriate said molar ratio of trifluoromethane and tetrafluoroethylene.

4. The process for preparing hexafluoropropylene from the pyrolysis of trifluoromethane and tetrafluoroethylene according to claim 2, wherein fresh trifluoromethane is added additionally to keep an appropriate said molar ratio of trifluoromethane and tetrafluoroethylene.

5. The process for preparing hexafluoropropylene from the pyrolysis of trifluoromethane and tetrafluoroethylene according to claim 1, wherein a quenching column is equipped at the exit of said reactor to prevent polymerization of HFP prepared at a high temperature to a solid polymer.

6. The process for preparing hexafluoropropylene from the pyrolysis of trifluoromethane and tetrafluoroethylene according to claim 2, wherein a quenching column is equipped at the exit of said reactor to prevent polymerization of HFP prepared at a high temperature to a solid polymer.

7. The process for preparing hexafluoropropylene from the pyrolysis of trifluoromethane and tetrafluoroethylene according to claim 3, wherein a quenching column is equipped at the exit of said reactor to prevent polymerization of HFP prepared at a high temperature to a solid polymer.

8. The process for preparing hexafluoropropylene from the pyrolysis of trifluoromethane and tetrafluoroethylene according to claim 4, wherein a quenching column is equipped at the exit of said reactor to prevent polymerization of HFP prepared at a high temperature to a solid polymer.

9. The process for preparing hexafluoropropylene from the pyrolysis of trifluoromethane and tetrafluoroethylene according to claim 1, wherein said apparatus for the pyrolysis of trifluoromethane and purification is comprised of a trifluoromethane cylinder, a tetrafluoroethylene cylinder, a mass flow controller, a pre-heater, a tube-type reactor, process water, a quenching column, condensing water, an acid reservoir, an acid washing column, a diaphram gas compressor, a dryer, a product reservoir, the first distillation column, a storage tank for an admixture of trifluoromethane and tetrafluoroethylene, the second distillation column, a HFP tank, a 6-port sampling valve, a gas chromatograph, and a computer.

10. The process for preparing hexafluoropropylene from the pyrolysis of trifluoromethane and tetrafluoroethylene according to claim 2, wherein said apparatus for the pyrolysis of trifluoromethane and purification is comprised of a trifluoromethane cylinder, a tetrafluoroethylene cylinder, a mass flow controller, a pre-heater, a tube-type reactor, process water, a quenching column, condensing water, an acid reservoir, an acid washing column, a diaphram gas compressor, a dryer, a product reservoir, the first distillation column, a storage tank for an admixture of trifluoromethane and tetrafluoroethylene, the second distillation column, a HFP tank, a 6-port sampling valve, a gas chromatograph, and a computer.

11. The process for preparing hexafluoropropylene from the pyrolysis of trifluoromethane and tetrafluoroethylene according to claim 3, wherein said apparatus for the pyrolysis of trifluoromethane and purification is comprised of a trifluoromethane cylinder, a tetrafluoroethylene cylinder, a mass flow controller, a pre-heater, a tube-type reactor, process water, a quenching column, condensing water, an acid reservoir, an acid washing column, a diaphram gas compressor, a dryer, a product reservoir, the first distillation column, a storage tank for an admixture of trifluoromethane and tetrafluoroethylene, the second distillation column, a HFP tank, a 6-port sampling valve, a gas chromatograph, and a computer.

12. The process for preparing hexafluoropropylene from the pyrolysis of trifluoromethane and tetrafluoroethylene according to claim 4, wherein said apparatus for the pyrolysis of trifluoromethane and purification is comprised of a trifluoromethane cylinder, a tetrafluoroethylene cylinder, a mass flow controller, a pre-heater, a tube-type reactor, process water, a quenching column, condensing water, an acid reservoir, an acid washing column, a diaphram gas compressor, a dryer, a product reservoir, the first distillation column, a storage tank for an admixture of trifluoromethane and tetrafluoroethylene, the second distillation column, a HFP tank, a 6-port sampling valve, a gas chromatograph, and a computer.

* * * * *

UNITED STATES PATENT AND TRADEMARK OFFICE
CERTIFICATE OF CORRECTION

PATENT NO.   : 6,403,848 B1
DATED        : June 11, 2002
INVENTOR(S)  : Dong Ju Moon et al.

It is certified that error appears in the above-identified patent and that said Letters Patent is hereby corrected as shown below:

Column 1,
Line 20, "from" should be deleted; and
Line 44, "has complicate" should read -- is a complicated --.

Column 4,
Line 6, "from" should be deleted; and
Line 21, "Hewllet" should read -- Hewlett --.

Column 7,
Line 62, "$RC_{318}$" should read -- RC318 --.

Column 8,
Line 22, "unlit" should read -- unit --.

Column 9,
Line 26, "diaphram" should read -- diaphragm --.

Signed and Sealed this

Fourteenth Day of January, 2003

JAMES E. ROGAN
*Director of the United States Patent and Trademark Office*